(12) United States Patent
Wieser et al.

(10) Patent No.: US 11,744,940 B2
(45) Date of Patent: Sep. 5, 2023

(54) DRUG DELIVERY DEVICE WITH NEEDLE ACTUATION MECHANISM

(71) Applicant: SENSILE MEDICAL AG, Olten (CH)

(72) Inventors: Oliver Wieser, Zürich (CH); Maximilian Marhöfer, Basel (CH)

(73) Assignee: SENSILE MEDICAL AG, Olten (CH)

( * ) Notice: Subject to any disclaimer, the term of this patent is extended or adjusted under 35 U.S.C. 154(b) by 451 days.

(21) Appl. No.: 17/057,728

(22) PCT Filed: May 22, 2019

(86) PCT No.: PCT/EP2019/063269
§ 371 (c)(1),
(2) Date: Nov. 23, 2020

(87) PCT Pub. No.: WO2019/228895
PCT Pub. Date: Dec. 5, 2019

(65) Prior Publication Data
US 2021/0369957 A1    Dec. 2, 2021

(30) Foreign Application Priority Data
May 28, 2018   (EP) .................................... 18174647

(51) Int. Cl.
*A61M 5/158*  (2006.01)
*A61M 5/142*  (2006.01)
*A61M 5/32*   (2006.01)

(52) U.S. Cl.
CPC ........ *A61M 5/158* (2013.01); *A61M 5/14212* (2013.01); *A61M 5/3221* (2013.01);
(Continued)

(58) Field of Classification Search
CPC .......... A61M 2005/3224; A61M 2005/14252; A61M 2005/14256; A61M 2005/1426;
(Continued)

(56) References Cited

U.S. PATENT DOCUMENTS 7,726,955 B2   6/2010  Ryser et al.
8,535,269 B2   9/2013  Scheurer et al.
(Continued)

FOREIGN PATENT DOCUMENTS

WO   WO 2005/039674   5/2005
WO   WO 2015/015379   2/2015

OTHER PUBLICATIONS

Written Opinion in International Application No. PCT/EP2019/063269, dated Aug. 9, 2019, pp. 1-8.

*Primary Examiner* — Kami A Bosworth
*Assistant Examiner* — Antarius S Daniel
(74) *Attorney, Agent, or Firm* — SALIWANCHIK, LLOYD & EISENSCHENK

(57) ABSTRACT

A drug delivery device (1) comprising a delivery unit (2) receiving a drug cartridge (3) containing a drug to be administered to a patient in need thereof, the delivery unit comprising a subcutaneous delivery mechanism (7) including a needle (24), a needle support (8) to which the needle is mounted, and a needle actuation mechanism (9) configured to move the needle from a retracted position within a housing (5) of the delivery unit (2), to an extended delivery position where the needle projects through a base wall (14) of the housing. The needle actuation mechanism comprises a rotary actuator (10) configured to engage an engagement lever (11) coupled to the needle support (8) for translating the needle support between retracted and extended delivery positions.

28 Claims, 11 Drawing Sheets

(52) U.S. Cl.
CPC .............. *A61M 2005/1585* (2013.01); *A61M 2005/3224* (2013.01)

(58) Field of Classification Search
CPC ........ A61M 2005/1585; A61M 5/3232; A61M 5/3234; A61M 5/158
See application file for complete search history.

(56) References Cited

U.S. PATENT DOCUMENTS

| | | |
|---|---|---|
| 10,076,605 B2 | 9/2018 | Marbet et al. |
| 10,632,249 B2 | 4/2020 | Marbet et al. |
| 2005/0215951 A1* | 9/2005 | Saulenas ............ A61B 5/15003 604/110 |
| 2013/0338594 A1* | 12/2013 | Da Ros ................ A61M 5/158 604/164.12 |
| 2016/0008537 A1 | 1/2016 | Lanigan |
| 2016/0184512 A1* | 6/2016 | Marbet ............. A61M 5/14248 604/157 |
| 2016/0213838 A1 | 7/2016 | Schabbach et al. |

* cited by examiner

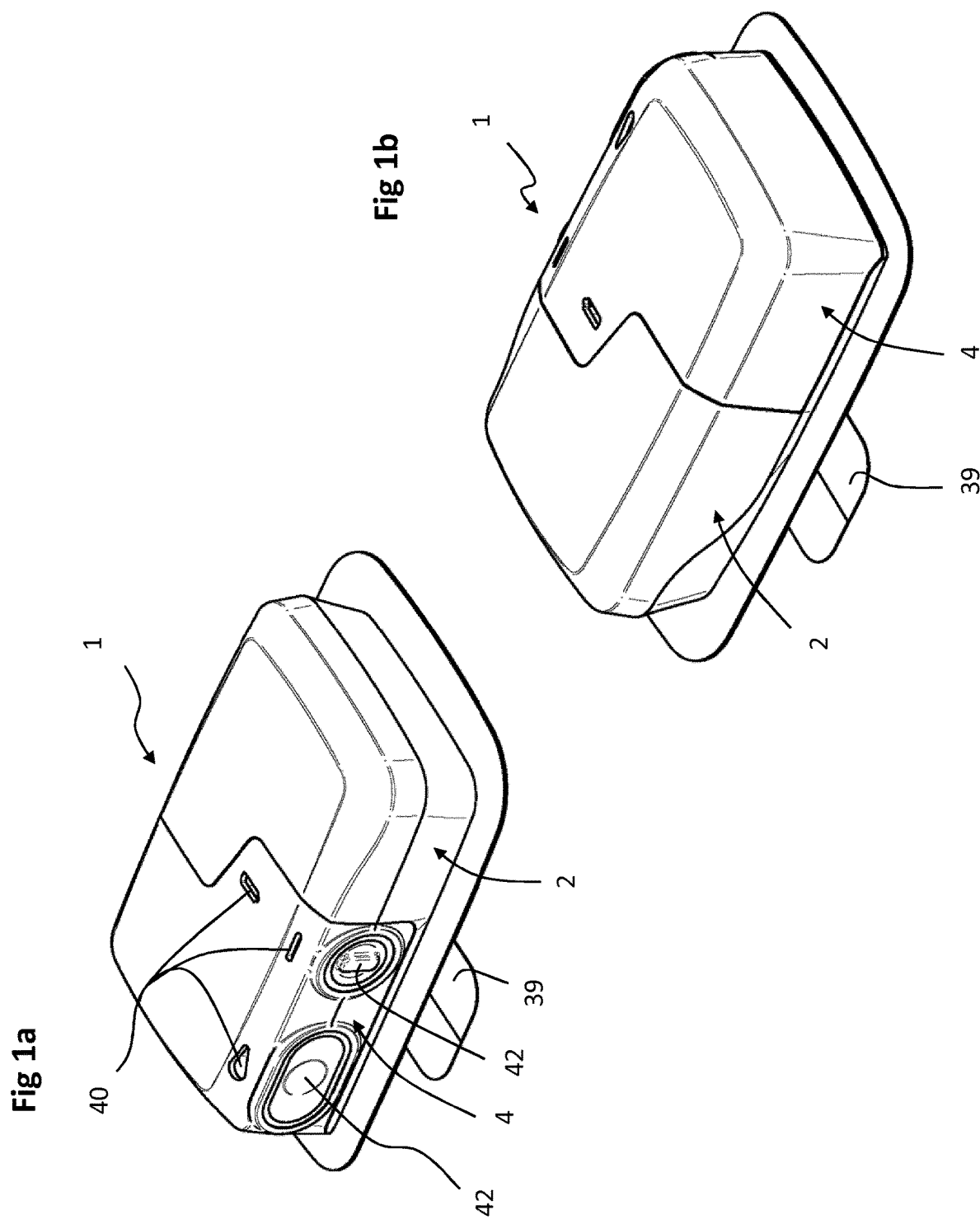

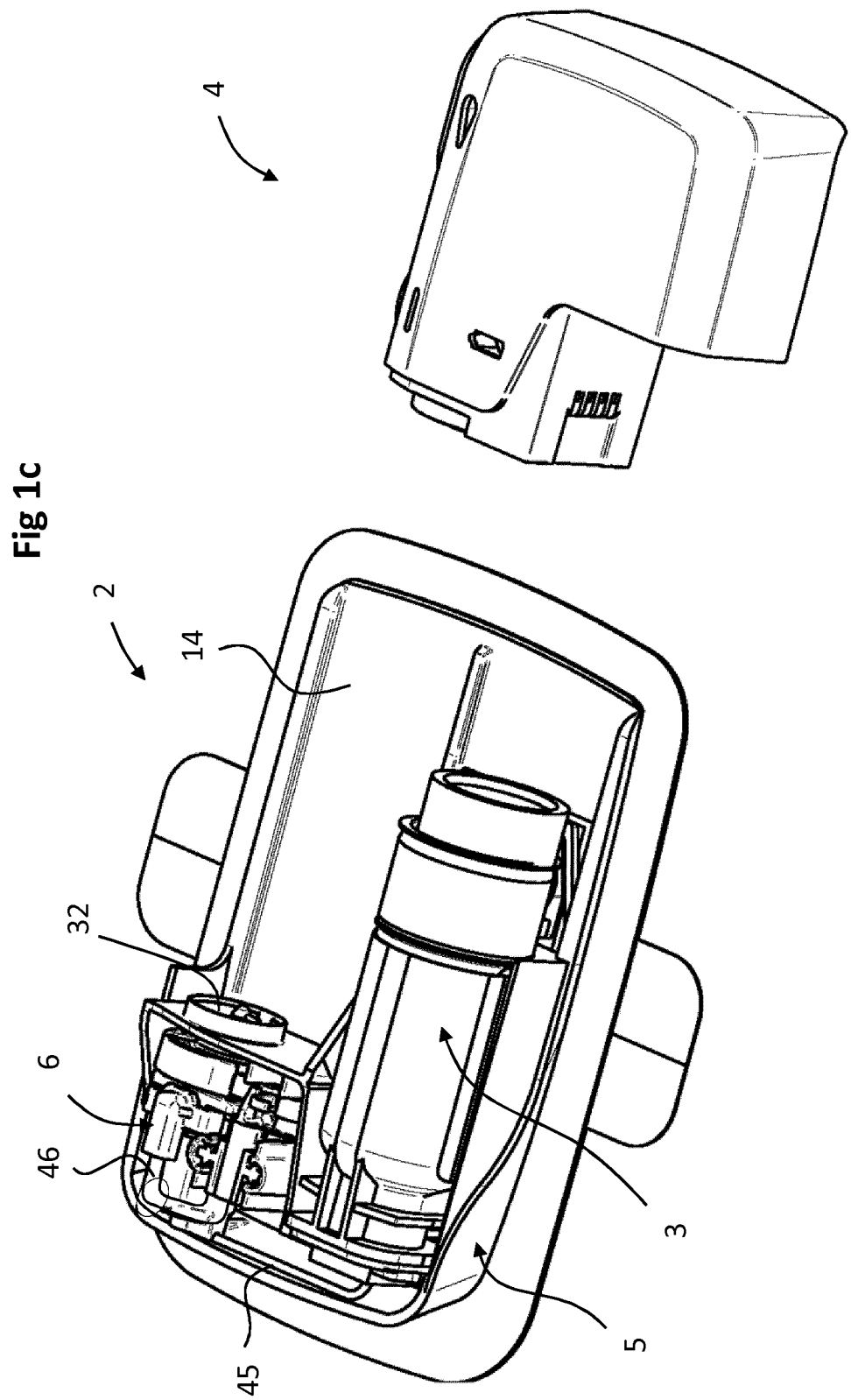

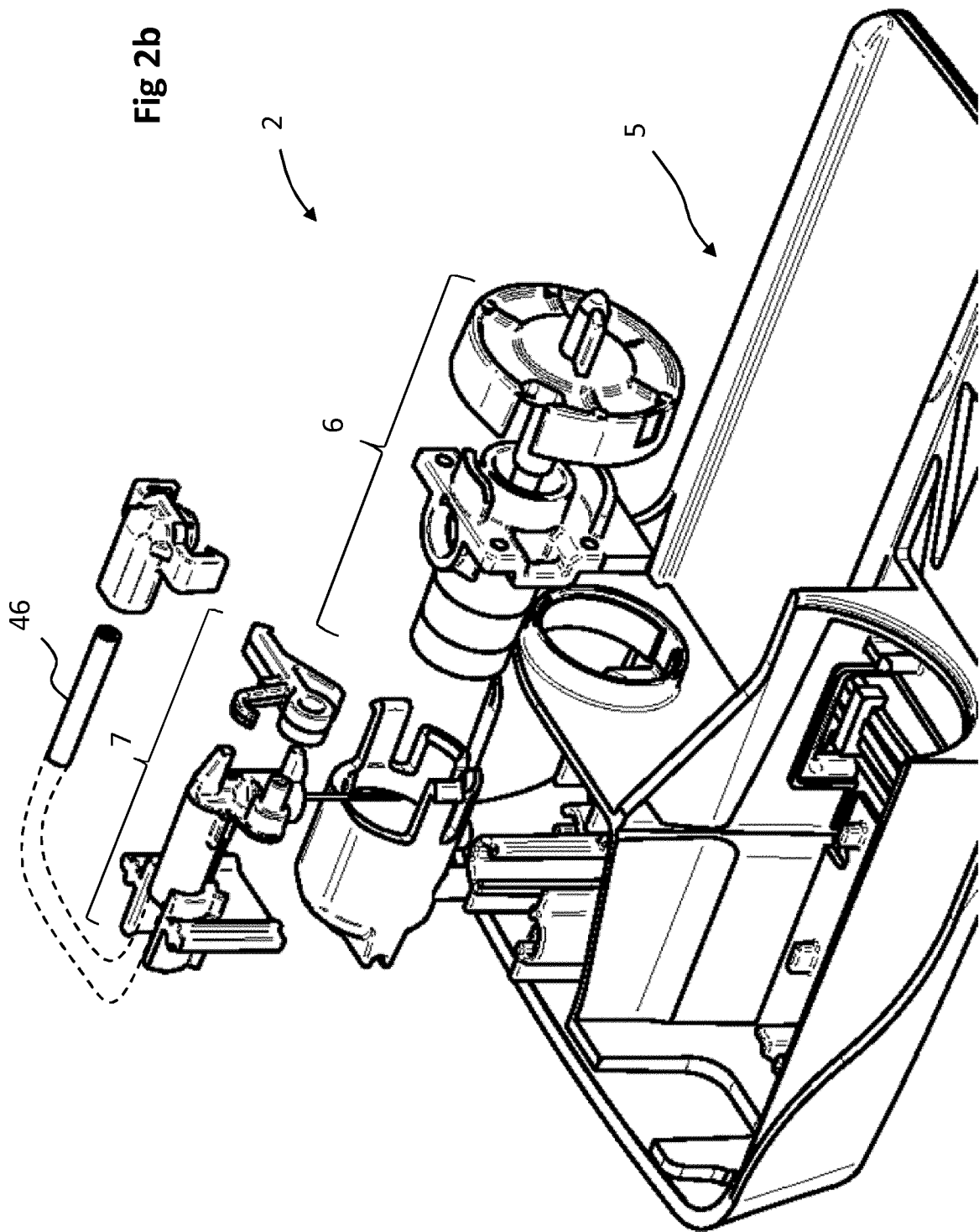

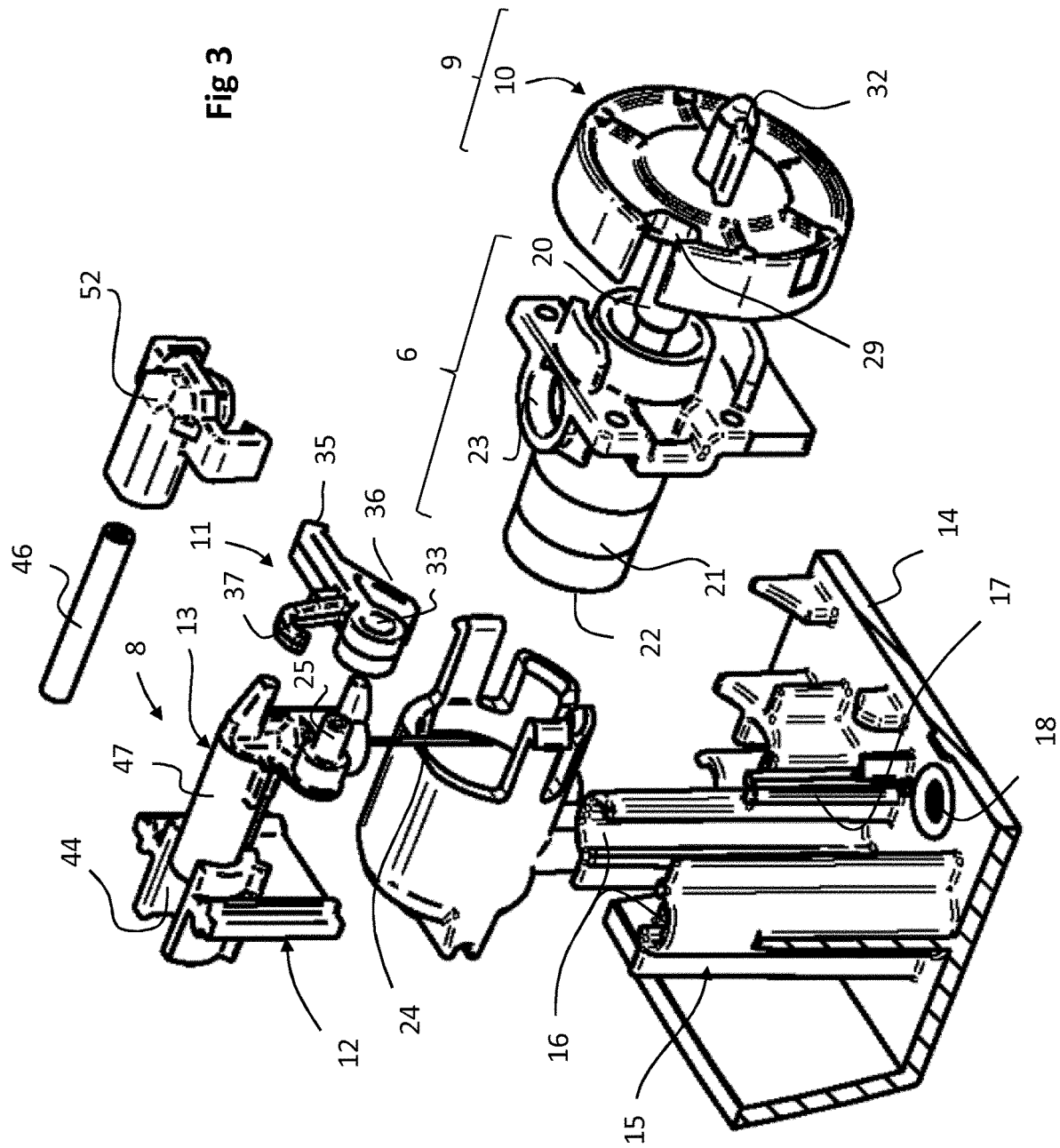

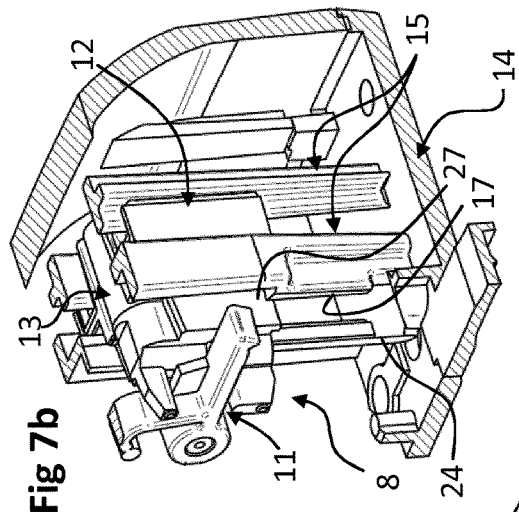
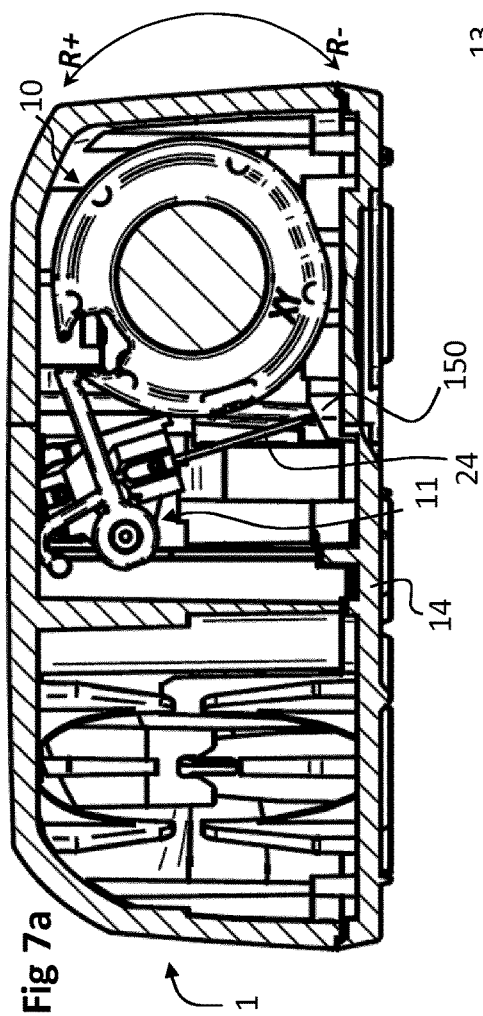
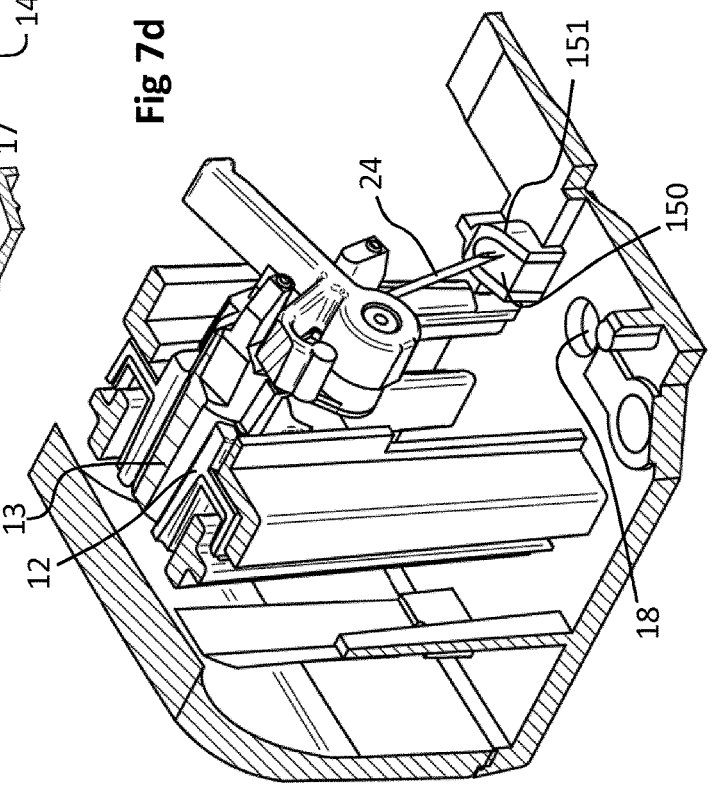
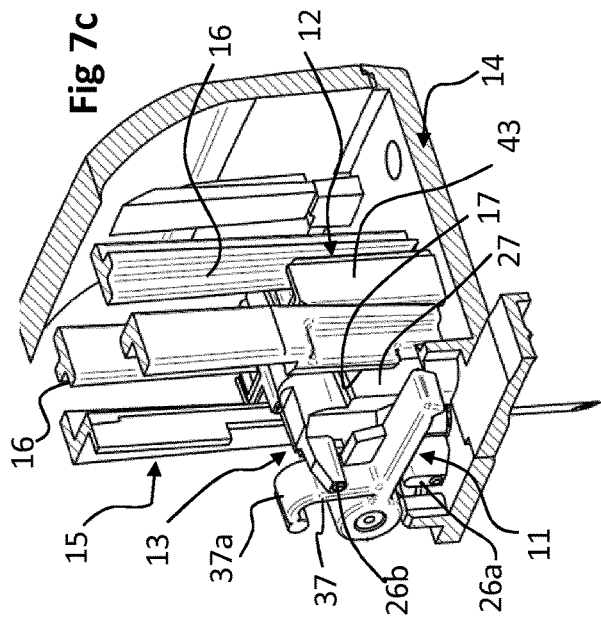

DRUG DELIVERY DEVICE WITH NEEDLE ACTUATION MECHANISM

CROSS-REFERENCE TO RELATED APPLICATION

This application is the U.S. national stage application of International Patent Application No. PCT/EP2019/063269, filed May 22, 2019.

TECHNICAL FIELD

This invention relates to a drug delivery device for transcutaneous delivery of a liquid drug, with a needle actuation mechanism.

DESCRIPTION OF RELATED ART

A drug delivery device with a needle actuation mechanism is described in WO2015015379. The needle actuation mechanism in the drug delivery device described in the aforementioned document advantageously provides a reliable and safe needle actuation mechanism that can be actuated by a pump drive and that does not require overcoming high spring forces of a pre-stressed spring, or a complex mechanism for engagement and retraction of the needle.

Nevertheless a drawback of the aforementioned needle actuation mechanism in certain applications is that the lever arm requires a certain size for efficient operation. For very small drug delivery devices such as small patch devices, in particular for drugs that are pumped in very small quantities such as concentrated insulin, the aforementioned mechanism is not sufficiently compact.

U.S. Pat. No. 8,535,269 describes a needle actuation system for a drug delivery device having a needle that is mounted on a rotatable support and that is rotated from the protected position to an active position where the needle can then be inserted into a patient's skin. After retraction of the needle after the use of the device, the needle may be pivoted into a protected position. This mechanism is however bulky and complicated, which may thus also adversely affect the reliability and safety of the device. Moreover, the provision of the needle in a protected position prior to use, requiring rotation of the needle to an active position prior to use, increases the complexity of the actuation of the device, making it not well adapted for automated insertion by motorized actuation means.

It would therefore be advantageous to benefit from the advantages of a simple and reliable needle actuation mechanism yet provide this in a particularly compact configuration.

It is also desirable to ensure the safety of the device, in particular of the disposable portions of the drug delivery device that should be prevented from be re-used once they have been used.

SUMMARY OF THE INVENTION

In view of the foregoing, an object of the invention is to provide a drug delivery device with a needle actuation mechanism that is compact, safe, and reliable.

It is advantageous to provide a drug delivery device that is economical to produce.

It is advantageous to provide a drug delivery device that is comfortable to wear and easy to use.

Objects of the invention are achieved by a drug delivery device according to claim 1.

Objects of the invention are achieved by a drug delivery device according to claim 3.

Disclosed herein is a drug delivery device comprising a delivery unit receiving a drug cartridge containing a drug to be administered to a patient in need thereof, the delivery unit comprising a subcutaneous delivery mechanism including a needle, a needle support to which the needle is mounted, and a needle actuation mechanism configured to move the needle from a retracted position within a housing of the delivery unit, to an extended delivery position where the needle projects through a base wall of the housing, the needle actuation mechanism comprising a rotary actuator configured to engage an engagement lever coupled to the needle support for translating the needle support between retracted and extended delivery positions.

According to a first aspect of the invention, the needle support comprises a translation guide member slidably mounted with respect to the housing, and a rotation guide member rotatably mounted to the translation guide member, the needle being fixed to the rotation guide member configured to tilt the needle in a fully retracted park position after full retraction of the needle.

According to a second aspect of the invention, the engagement lever is pivotally mounted on the needle support and elastically engages the needle support configured to allow the engagement lever to elastically pivot and bias against the rotary actuator of the needle actuation mechanism in the fully extended delivery position such that the rotary actuator may turn freely in a delivery direction (R+).

In an advantageous embodiment, the needle support comprises a translation guide member slidably mounted with respect to the housing, and a rotation guide member rotatably mounted to the translation guide member, the needle being fixed to the rotation guide member configured to tilt the needle in a fully retracted park position after full retraction of the needle.

In an advantageous embodiment, the rotary actuator is coupled directly to a rotor of a pump module mounted in the delivery unit.

In an advantageous embodiment, the rotary actuator is integrally formed with the pump module rotor.

In an advantageous embodiment, the rotary actuator comprises a disc shape with an outer peripheral rim comprising a catch formed by a recess in the rim for engaging an engagement end of the engagement lever.

In an advantageous embodiment, the engagement lever comprises a suspension biasing against the needle support for elastic pivoting of the engagement lever relative to the needle support.

In an advantageous embodiment, the rotation guide member comprises a cylindrical body portion rotatably mounted in a rotation member support of the translation guide member.

In an advantageous embodiment, the rotation guide member of the needle support comprises a liquid channel therein interconnecting a liquid delivery conduit connected to an outlet of the pump module to the hollow needle.

In an advantageous embodiment, the engagement lever comprises a protuberance on a lower side of the engagement end configured for catching on a lower catch edge of the rotary actuator when it moves in a reverse direction (R−) for moving the needle from the extended delivery position to the retracted position.

In an advantageous embodiment, the engagement lever comprises a pivot portion and an engagement arm extending from the pivot portion to the engagement end, the pivot portion being mounted on a pivot support extending from the rotation guide member of the needle support.

In an advantageous embodiment, the rotation guide member of the needle support comprises an anti-rotation guide surface slidably engaging a complementary anti-rotation guide surface extending from the housing base wall configured for preventing rotation of the rotation guide member when travelling between the initial retracted position and the extended delivery position, the anti-rotation surfaces arranged to disengage in the fully retracted park position when the rotary actuator is rotated in a reverse direction to allow tilting of the needle into a fully retracted park position preventing further reuse of the needle.

In an advantageous embodiment, the tip of the needle in the fully retracted park position engages a locking element that blocks the needle in the fully retracted park position.

In an advantageous embodiment, the locking element comprises a locking nest filled with a soft material into which the tip of the needle buries when moving into the fully retracted park position. The soft material may advantageously comprise a thermoplastic elastomer.

In an advantageous embodiment, the locking element comprises a locking protrusion upstanding from the housing base wall, over which the tip of the needle and is blocked thereby in the tilted park position.

In an advantageous embodiment, the rotary actuator comprises a drive interface configured for coupling to a drive mounted in a base unit comprising an electronic control system, a power source and said pump drive for actuation of the rotary actuator.

In an advantageous embodiment, the delivery unit is formed as a disposable part containing said drug cartridge in a housing of the delivery unit, and a base unit formed as a reusable part comprising an electronic control system, a power source, and a pump drive, the base unit being removable mountable to the delivery unit.

In an advantageous embodiment, the delivery unit comprises a mounting surface with an adhesive layer on an underside of the base wall from mounting against a patient's skin, the drug delivery device formed as a patch device.

Further objects and advantageous features of the invention will be apparent from the claims, from the detailed description, and annexed drawings, in which:

BRIEF DESCRIPTION OF THE DRAWINGS

FIG. 1a is a perspective view of an embodiment of a drug delivery device according to the invention;

FIG. 1b is a view similar to FIG. 1a from another side of the device;

FIG. 1c is a perspective view of the device of FIGS. 1a and 1b showing a base unit uncoupled from a delivery unit, a cover portion of the delivery unit being removed to better see the inside of the delivery unit;

FIG. 2b is a view similar to FIG. 2a showing some components of the drug delivery unit in exploded fashion;

FIG. 3 is an exploded view of components of the delivery unit according to an embodiment of the invention, showing inter alia a pump module and a subcutaneous delivery mechanism of the delivery unit;

FIGS. 7a to 7d are views of the drug delivery according to another embodiment of the invention, where FIG. 7a is a cross-sectional view showing the needle actuation system in a fully retracted and tilted park position, and FIGS. 7b to 7d are perspective partial views of the needle support and needle actuation mechanism in an initial state prior to first use (FIG. 7b), an extended delivery position (FIG. 7c) and a fully retracted and tilted park position (FIG. 7d).

DETAILED DESCRIPTION OF EXEMPLARY EMBODIMENTS

Figure 2A:
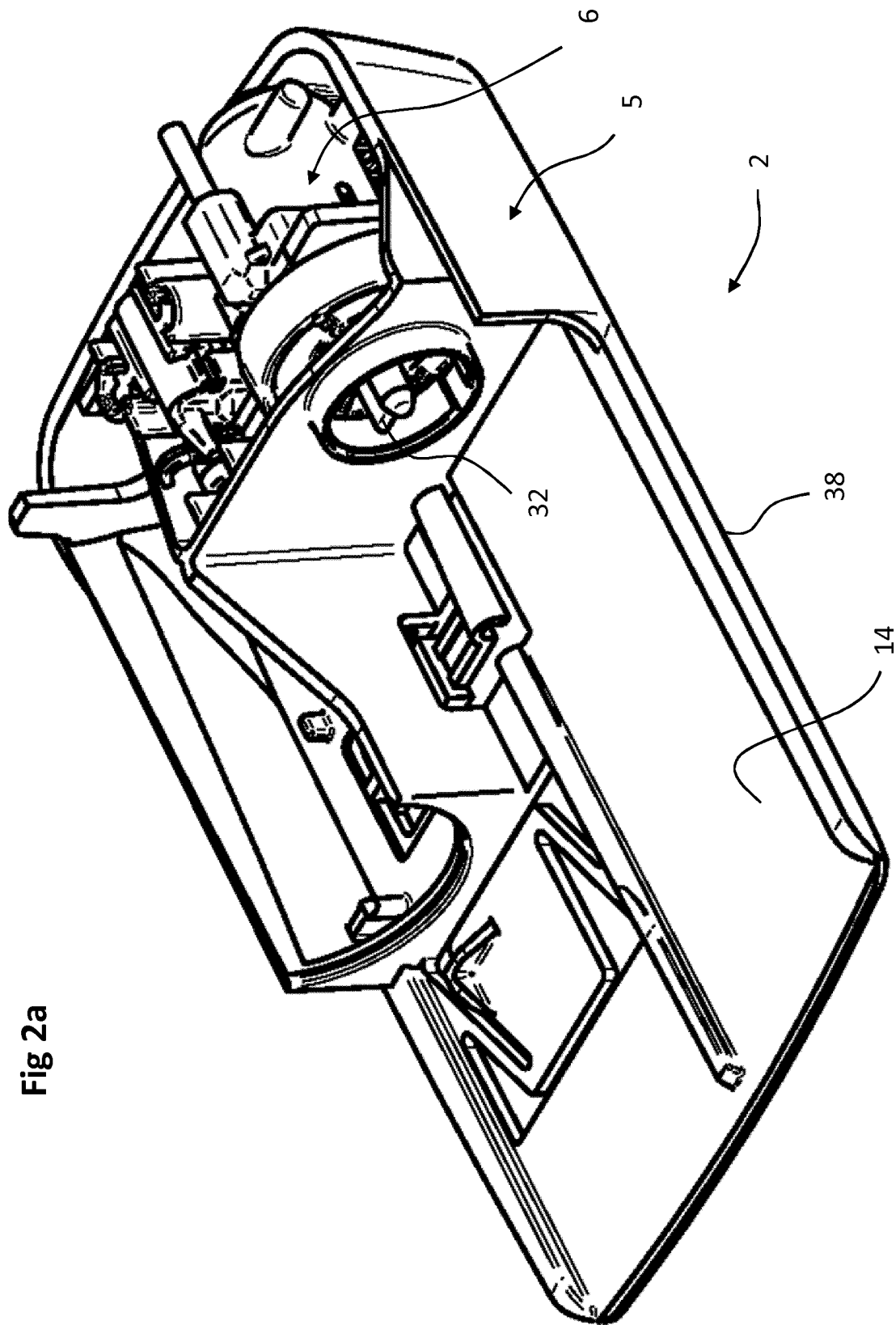
FIG. 2a is a perspective view of the delivery unit of the device of FIGS. 1a to 1c with a cover portion partially removed and without a drug cartridge mounted therein.

Referring to the figures, and in particular to FIGS. 1-4, a drug delivery device 1 comprises a delivery unit 2 and a base unit 4. In an embodiment, the delivery unit 2 is a disposable unit 2 and is removably connected to the base unit 4 which may be re-usable, although it will be appreciated that in other embodiments the base may be formed with the delivery unit as a single disposable unit.

The delivery unit 2 comprises a subcutaneous delivery mechanism 7 to deliver a fluid transdermally, a drug cartridge 3 with a reservoir containing the fluid to be administered to a patient, a pump 6 to transfer the fluid from the reservoir to the subcutaneous delivery mechanism 7, and a support member or housing 5 for supporting the aforementioned components. A supply conduit 45 fluidly connects the outlet of the drug cartridge 3 to the inlet 20 of the pump module 6.

The base unit 4 comprises a pump drive (not shown), a battery (not shown), an electronic control unit (not shown) and a housing. The base unit housing may accommodate a portion of the reservoir when coupled to the delivery unit 2 and optionally comprise one or more sensors for detecting the drug fill level of the reservoir.

The pump module 6 is operable to pump fluid from the drug cartridge to a needle 24 for subcutaneous delivery. In this example the pump module comprises a drive interface 32 configured to couple rotationally with a pump drive mounted in the base unit 4 such that torque from the pump drive is transferred to the pump module to drive a rotor 20 of the pump in rotation. A suitable pump engine and drive unit is provided in WO 2005/039674, which is incorporated herein by reference. However, it will be appreciated that other rotary pump engines and pump drives may be used. Moreover, the pump engine could be permanently coupled or attached to a pump drive, and/or the drive could be incorporated in the delivery unit 2 and receive power, for instance via electrical contacts or by induction from a power source (not shown) mounted in the base unit 4.

An inlet 22 of the pump module 6 receives fluid from the supply conduit 45 and an outlet 23 of the pump supplies fluid to the needle 24 via a delivery conduit 46.

A rotary actuator 10 of a needle actuation mechanism 9 is, in an advantageous embodiment, mounted to the pump module 6 such that rotation of the pump rotor by the pump drive causes rotation of the rotary actuator 10, as will be discussed in more detail in the following. It will be appreciated that in other embodiments the rotary actuator may not be mounted directly onto the pump module, for example it may be coupled to the pump module via a geared system, or may alternatively be driven separately from the drive coupled to pump module 6, for instance by an independent motor or mechanism.

The subcutaneous delivery mechanism 7 comprises a needle support 8 and a needle 24 mounted to the needle support adapted for trans-dermal delivery of the fluid from the drug cartridge. The subcutaneous delivery mechanism 7 further comprises a needle actuation mechanism 9.

Figure 5A:
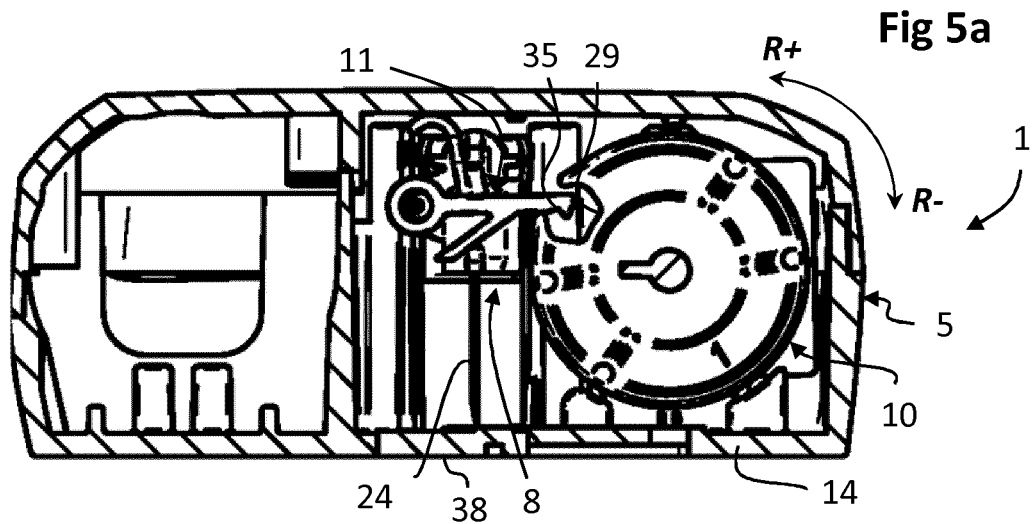
FIGS. 5a to 5c are cross sectional views of the drug delivery device illustrating a sequence of actions of the needle actuation mechanism according to an embodiment to the invention, FIG. 5a showing the needle actuation mechanism in an initial state prior to first use, FIG. 5b showing the needle actuation mechanism in an extended delivery position, FIG. 5c showing the needle actuation system in a fully retracted and tilted park position.
Figure 5B:
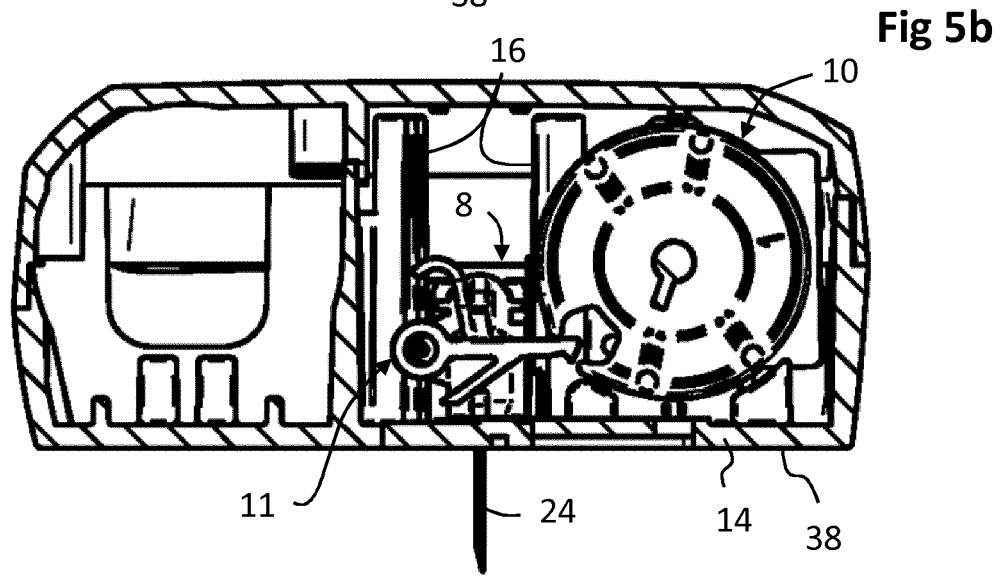
Figure 6A:
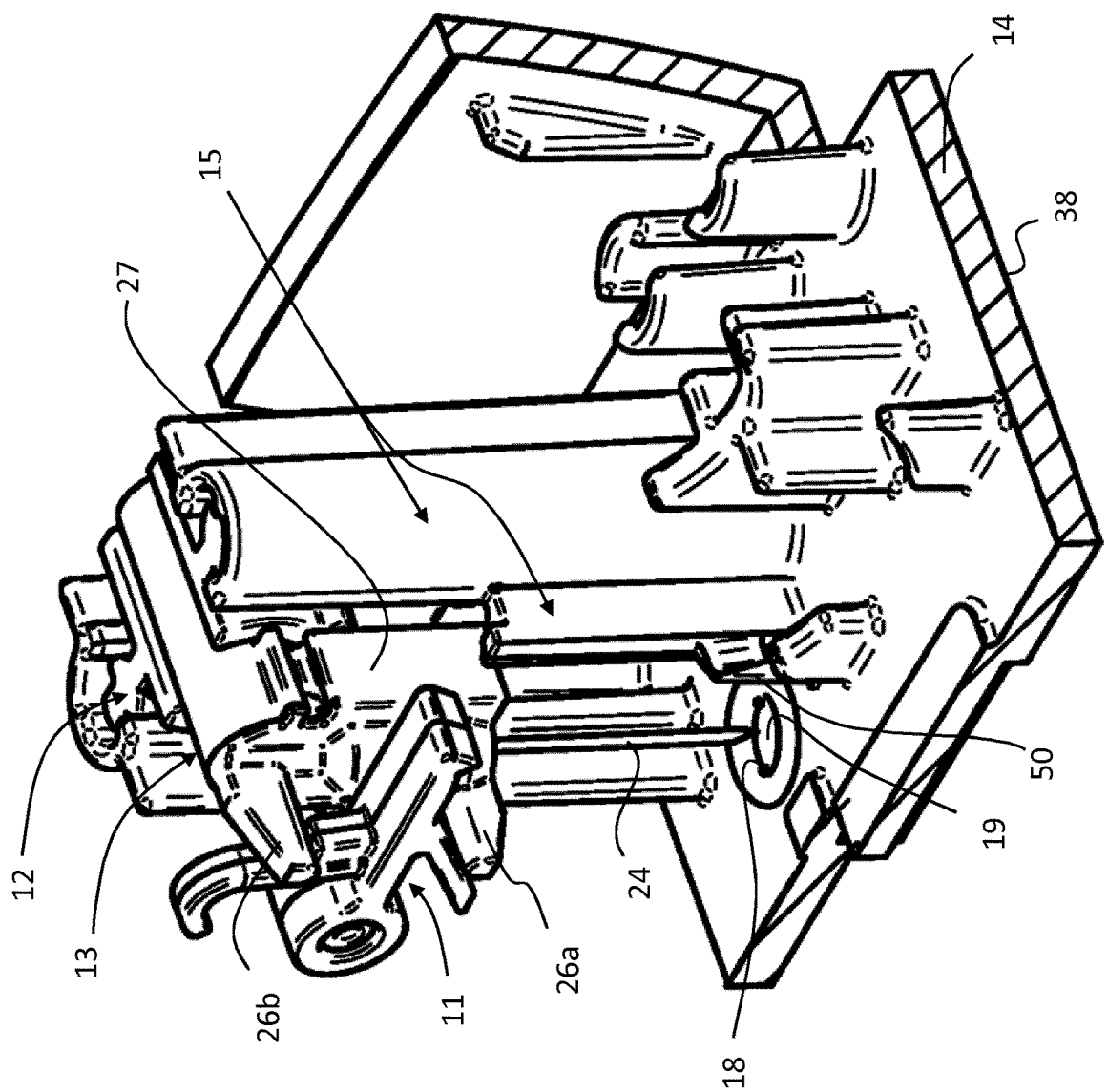
FIGS. 6a to 6c are perspective views of a needle support of the subcutaneous delivery mechanism in positions corresponding to FIGS. 5a to 5c respectively.
Figure 6B:
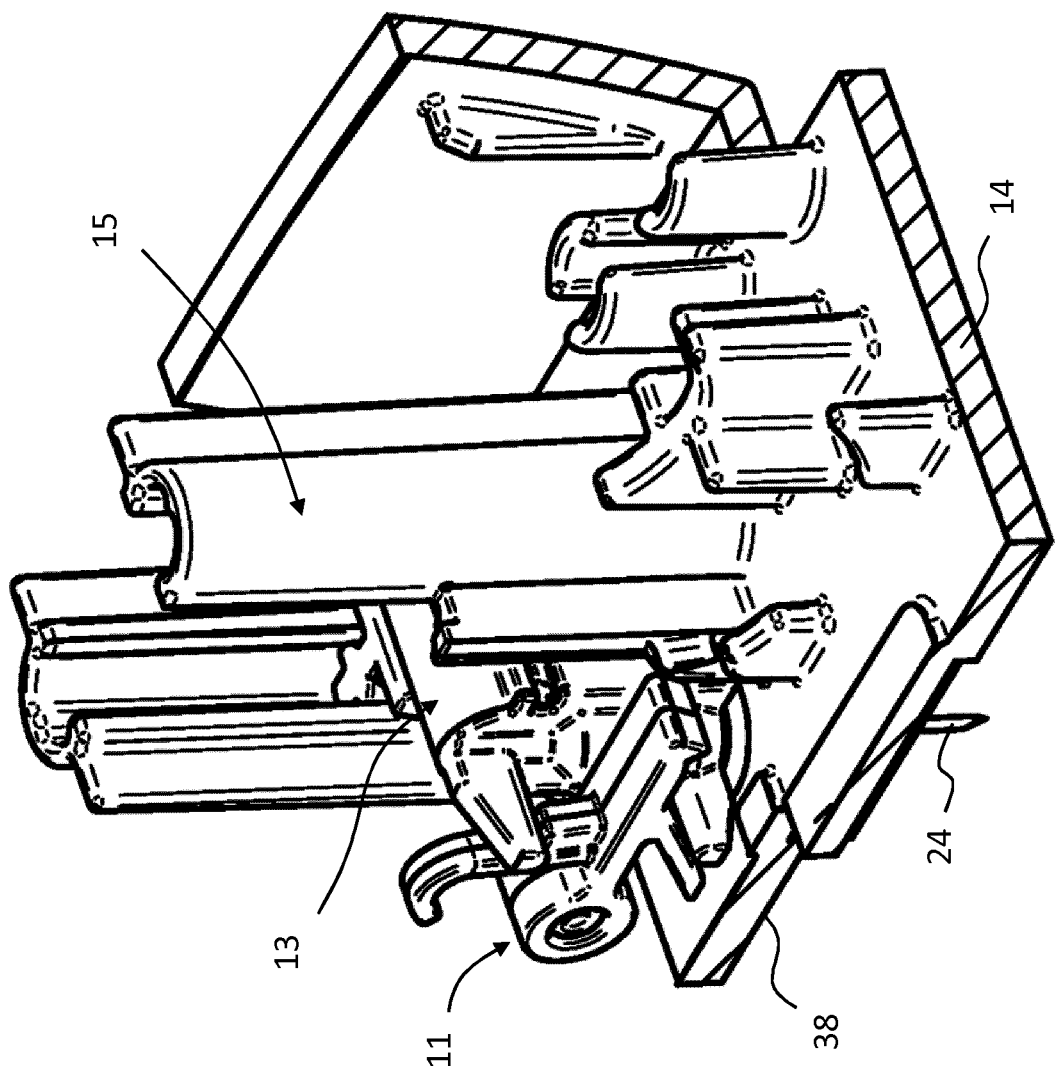

The needle support 8 comprises a translation guide member 12 that is slidably mounted on a needle support guide 15 fixed to the housing 5, in particular upstanding from the base wall 14 of the housing 5. The needle support guide 15 comprises translation guide rails 16 that slidably engage with guide rails 43 formed on the translation guide member 12 of the needle support 8. The complementary translation guide rail 16 and translation guide rails 43 allow slidable movement of the needle support 8 relative to the base wall 14 of the housing 5 such that the needle 24 can be translated from a retracted position within the housing as illustrated in FIG. 5*a* and FIG. 6*a*, to a delivery position extending through the base wall 14 of the housing as illustrated in FIG. 5*b* and FIG. 6*b* for a transdermal administration of the liquid drug to a patient.

Figure 5C:
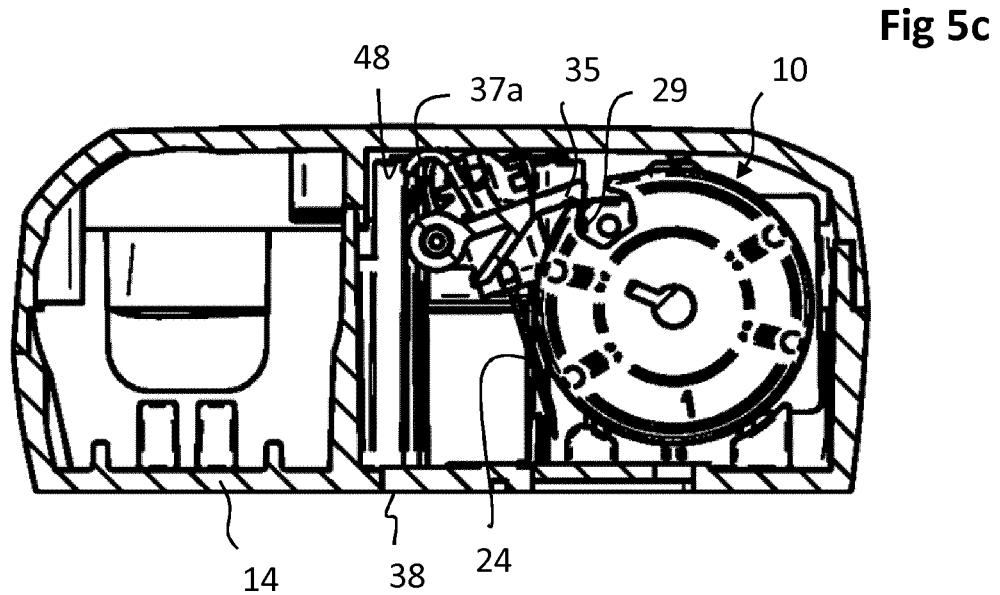
Figure 6C:
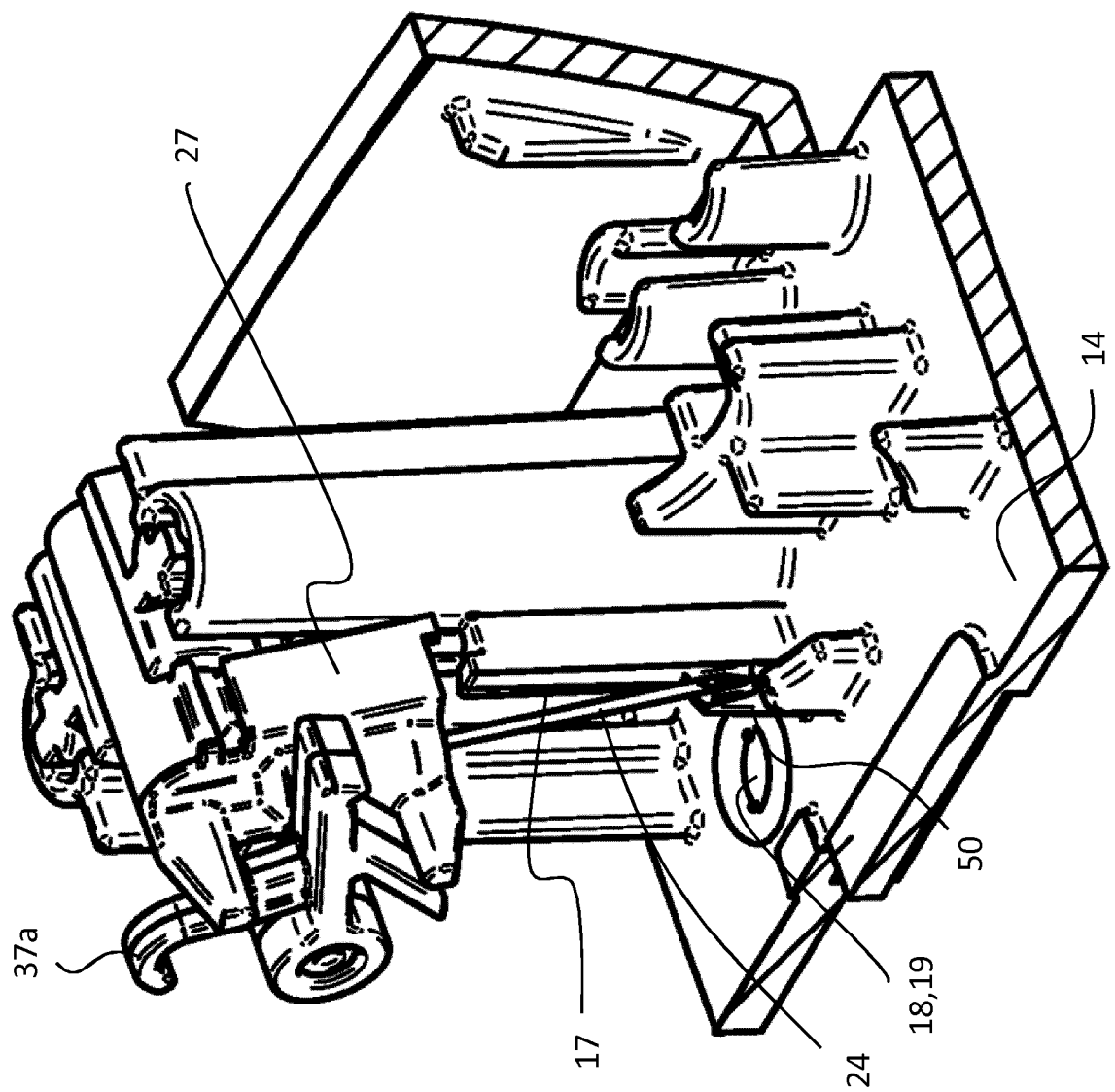

The needle support 8 further comprises a rotation guide member 13 that is rotatably mounted to the translation guide member 12, the needle 24 being fixed to the rotation guide member 13. The rotation guide member 13 allows the needle 24 to be rotated from the retracted position illustrated in FIGS. 5*a* and 6*a* to a fully retracted and tilted park position as illustrated in FIGS. 5*c* and 6*c* that disengages the actuation mechanism 9, thus preventing further use of the drug delivery device. the fully retracted and tilted park position illustrated in FIGS. 5*c* and 6*c* correspond to an end-of-use park position in which the disposable delivery unit may no longer be reused and would need to be replaced by a new delivery unit. In the end-of-use park position illustrated in FIGS. 5*c* and 6*c*, the needle 24 can no longer be engaged by the actuation mechanism 9 for return to the extended delivery position, thus ensuring the safety of the drug delivery device after use of the delivery unit.

The translation guide member 12 comprises a rotation member support 44 forming a bearing supporting a body 47, for instance a cylindrically shaped body 47 to allow rotation of the rotation guide member 13 relative to the translation guide member 12 around a rotation axis A1.

A fluid channel is formed within the rotation body fluidly interconnecting the hollow needle 24 to an inlet on the body 47 connected to a delivery conduit 46 connected via a connector 52 to the pump module outlet 23. The conduit 46 is supple enough to allow the relative rotation between the rotation guide member 13 and the housing 5.

The rotation guide member 13 is coupled to an engagement lever 11 of the needle actuation mechanism 9. The engagement lever 11 is in the illustrated embodiment and in a preferred mode of execution, rotatably mounted to the rotation guide member 13. Within the scope of the invention, the engagement lever may however also be fixedly mounted to the rotation guide member and in a variant integrally formed with the rotation guide member.

In the illustrated embodiment, the engagement lever 11 comprises a pivot portion 33 rotatably mounted on a pivot support 25 extending from the rotation guide member 13, and an engagement arm 34 extending from the pivot portion 33 to an engagement end 35. The engagement end 35 is configured to be engaged by a rotary actuator 10 of the needle actuation mechanism 9.

The rotary actuator 10, which in the illustrated embodiment is essentially in the form of a disc or wheel with a circumferential outer rim 28, is provided with a catch 29 that engaged the engagement end 35 when the rotary member is rotated. The catch 29 is formed by a recess or notch 30 in the rim 28 thus presenting catch edges 31*a*, 31*b* which engage respectively an upper surface and lower surface of the engagement end 35. The engagement end 35 in the retracted and extended positions as shown in FIGS. 5*a* and 5*b* and 6*a* and 6*b* extends into the notch 30.

It will be appreciated however that the rotary actuator may have various other forms and shapes providing an element that pushes down on the engagement lever 11 when moving from the retracted to extended position, respectively having an element that engages the engagement lever to move the lever upwards from the extended to the retracted positions, and the engagement end may also have various shapes and forms complementary to the catch of the rotary actuator for effecting the aforementioned movements.

In an advantageous embodiment, the rotary actuator 10 is coupled to the rotor 20 of the pump module 6 and may be integrally formed as a single part with the pump module rotor 20. Further, in an advantageous embodiment the rotary actuator 10 may comprise a drive interface 32 for coupling in rotation to a drive (not shown) mounted in the base unit 4. When the disposable unit 2 is coupled to the base unit 4, the drive interface 32 engages a complementary interface of the drive in the base unit. The rotary actuator may thus be driven in rotation by the pump drive, simultaneously with the rotor of the pump module.

As best seen in FIG. 5*a*, in a retracted position prior to first use of the delivery unit 2, the needle support 8 is in a retracted position with the needle 24 fully positioned within the housing 5 above the base wall 14. The engagement end 35 is in a position for engagement with the catch 29 of the rotary actuator 10, whereby in the illustrated embodiment the engagement end 35 is positioned within the recess or notch 30.

To use the drug delivery device 1, the delivery unit 2 is coupled and mounted to the base unit 4 such that the pump drive engages the drive interface 32 of the rotary actuator 10. In an embodiment where the delivery unit is provided with an adhesive base the protective film 39 is peeled off and the mounting surface 38 of the base will be placed against the patient's skin. It may however be noted that in other embodiments, the base wall may be provided without an adhesive layer and the device placed against the patient's skin by other means for instance by means of a strap or band encircling the patient's body portion against which the drug delivery device is placed. Upon initial use of the drug delivery device, for instance upon a first command to deliver a dose of liquid drug subcutaneously, whereby the initial dose may be setting a basal rate of a drug delivery or a bolus injection, the pump drive is actuated to turn the rotary actuator in a rotation direction that engages the engagement lever 11 and displaces it in translation from the retracted position to an extended delivery position as illustrated in FIGS. 5*b* and 6*b* such that the needle 24 pierces through the patient's skin and is in a position ready for delivery of the liquid drug trans-dermally.

In the illustrated embodiment, in the extended delivery position, the rotary actuator may continue rotating in the delivery direction R+. In the delivery direction R+ the upper engagement edge 31*b* of the catch 29 is configured to be able to move past the engagement end 35 such that the rotary actuator 10 may turn in the delivery direction continuously once the needle is the extended position without being blocked by the engagement lever 11.

The engagement lever 11 may further be provided with a suspension coupling the lever to the rotation guide member 13.

Figure 4:
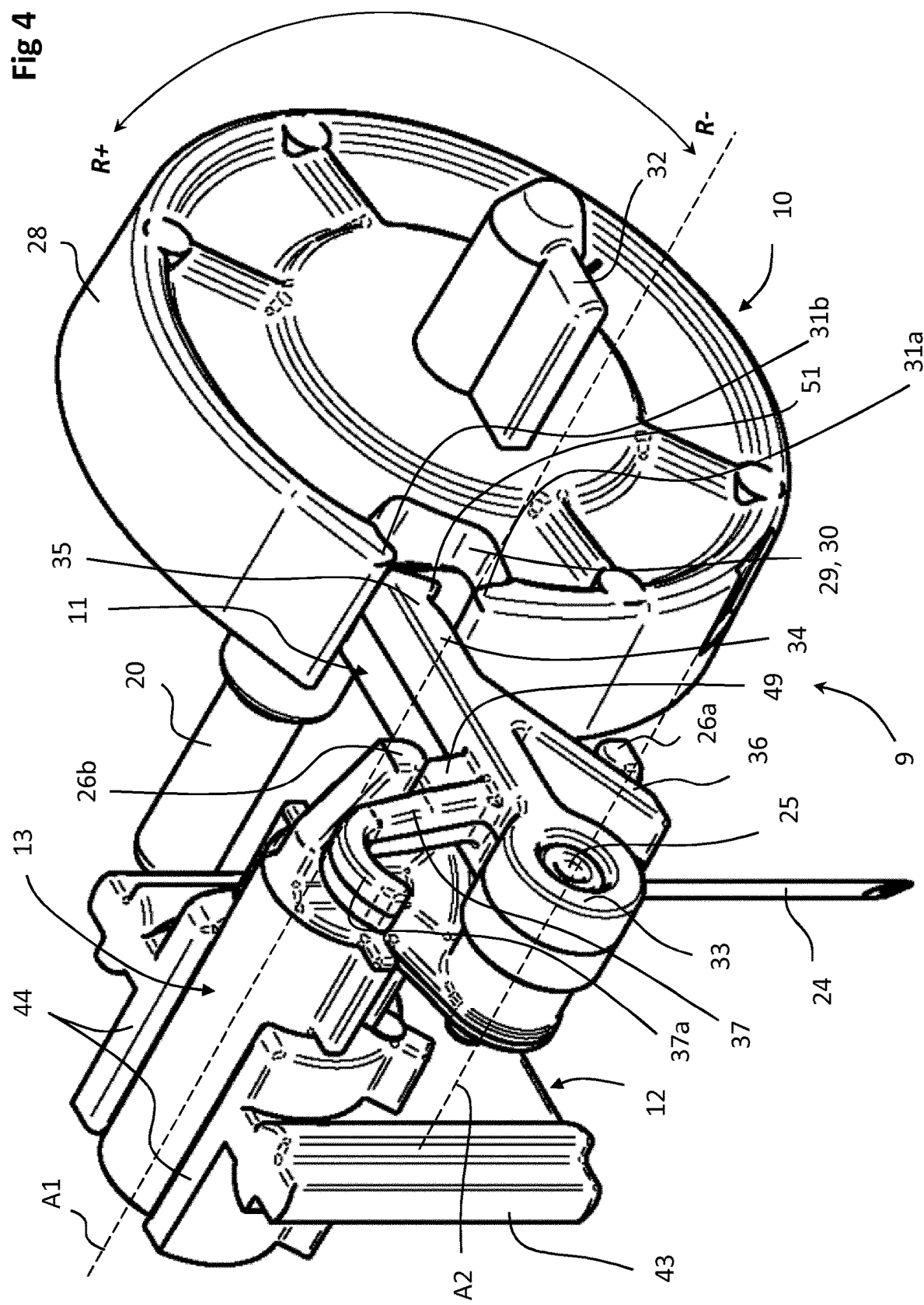
FIG. 4 is a perspective view of a subcutaneous delivery mechanism of a delivery unit according to an embodiment of the invention.

In the variant illustrated in FIG. 4, the suspension comprises a lower suspension arm 36 extending from the engagement lever biasing against a lower abutment shoulder 26a extending from the rotation guide member 13 configured to allow limited elastic rotation of the engagement lever relative to the rotation guide member 13 by elastic bending of the suspension arm 36.

This allows the rotary actuator 10 to be in contact with and press slightly against the engagement end 35 of the engagement lever 11 while turning in the delivery direction R+ without affecting the position of the needle during delivery of a drug.

In a variant, instead of a lower suspension arm 36 extending from the engagement lever 11, other elastic means may be provided, for instance the engagement lever 11 may have a certain elasticity to allow flexible bending thereof sufficient to accommodate contact with the rotary actuator during rotation in the delivery direction R+.

In the variant illustrated in FIGS. 7a to 7d, there is no lower suspension arm and the elasticity of the engagement lever 11 and of the suspension arm 37 pressing against the upper abutment shoulder 26b is configured to allow controlled flexible bending of the engagement lever to accommodate contact with the rotary actuator during rotation in the delivery direction R+ without affecting the position of the needle during delivery of a drug.

In a variant, the spring suspension element may extend from the rotation guide member 13 and press against a rigid engagement lever 11, or in the further variant elastic members may be provided on both the rotation guide member and the engagement lever that inter-engage. In further variant, the engagement lever may be integrally formed with the rotation guide member 13, for instance as a single injected part, with flexible connecting elements between the engagement lever and other portions of the rotation guide members that enable a certain flexible bending thereof configured to allow contact during rotation in the delivery position yet with sufficient engagement resistance to move the needle actuation mechanism from the retracted to the extended positions. In a variant, the elastic means may be connected to an upper portion of the lever or to a lower portion of the lever provided that the function of allowing certain flexibility in the delivery direction is provided as discussed above.

Once use of the delivery unit is finished, for instance when the drug cartridge is in an empty state, or after a maximum duration of use of the disposable delivery unit is reached, a command for retraction of the transcutaneous needle from the extended position to the retracted position is executed. During this operation, the pump drive is controlled to move in a reverse direction R− whereby the rotary actuator 10 moves in the reverse direction R−. In the reverse direction, a lower edge 31a of the catch 29 engages the engagement end 35 of the engagement lever 11 thus lifting up the needle support 8 from the extended to the retracted position. The engagement end may be provided with a hook protrusion or other complementary element with the lower catch edge 31a of the rotary actuator such that upon reverse direction the engagement lever is engaged by the catch and lifted upwards away from the base wall 14.

Rotation of the rotation guide member 13 is prevented by an anti-rotation guide surface 27 on the rotation guide member sliding along an anti-rotation guide surface 17 of the needle support guide 15 on the housing 5. The anti-rotation guide surface 17 may be formed as a surface upstanding from the base wall 14. During rotation in the reverse direction R− of the rotary actuator 10 past the initial retracted position prior to the first use illustrated in FIG. 5a, the needle support is further lifted away from the base wall 14 until the complementary anti-rotation guide surfaces 27, 17 disengage. At this moment continued rotation in the reverse direction of the rotary actuator 10 forces the rotation of the rotation guide member 13 into the fully retracted and tilted park position illustrated in FIGS. 5c and 6c in which it can no longer be reengaged thus preventing reuse of the delivery unit 2.

In the illustrated embodiments, when moving into the fully retracted park position, the tip of the needle 24 engages a locking element 50, 150 that blocks the needle in the fully retracted park position.

In the embodiment illustrated in FIGS. 6a to 6c, when moving into the fully retracted park position, the tip of the needle 24 slips over a locking protrusion 50, as best seen in FIG. 6c, and is then blocked and can no longer return to the unlocked position. The locking protrusion 50 is provided with a tapered surface on the side facing the orifice 18 to guide the needle tip as it presses elastically against the locking protrusion, and assist it to slip over the locking protrusion 50. Once in the fully retracted parked and locked position, the needle tip engages in a groove and can no longer slip back to the tapered entry side of the locking protrusion. The protuberance 51 on the tip of the engagement lever 35 is configured to assist in increasing the torque on the engagement lever 11 to allow the needle tip to slip over the locking protrusion.

In the embodiment illustrated in FIGS. 7a to 7d, when moving into the fully retracted park position, the tip of the needle 24 buries into a locking nest 150 filled with a soft material which catches the needle tip, as best seen in FIG. 7d, the needle being then blocked from returning to the unlocked position. The soft material may for instance be a soft polymeric compound, for instance a thermoplastic elastomer, thermoplastic rubber, liquid silicone rubber, or similar material, that may be molded or deposited in a nest wall 151 of the base 14. The soft material may advantageously be molded in the base of the housing during the base molding process, in a two component molding process as per se known in the art of injection molding.

In the illustrated embodiments, an upper suspension arm 37 extends from the engagement lever 11 and has a curved flexible end 37a that this configured to biased against an upper surface 48 of the housing 5. The upper arm defines the initial position prior to first use as illustrated in FIG. 5a and prevents upward sliding of the needle support in the initial position. In the fully retracted park position, the upper arm may optionally also serve to block rotation of the rotation guide member 13 from the retracted tilted position back to a non-tilted position. The upper arm 37 may also serve to limit the flexible pivoting of the engagement lever during actuation and use by abutting against the abutment 26b on the rotation guide member 13.

In an alternative variant, the needle 24 is employed for inserting a flexible cannula tube transdermally, the needle being retracted to the fully retracted park position as illustrated in FIGS. 5c and 6c before first administration of a drug. In this alternative embodiment, the needle does not need to be hollow and is not connected to the outlet of the pump module. The outlet of the pump module in such configuration is connected to via a liquid coupling that closes the orifice through which the needle extends when retracted, for instance in a form of a septum or valve such that after retraction of the needle, liquid pumped by the pump flows through the cannula that extends transdermally through the patient's skin. The soft cannula may increase comfort of wearing the drug delivery device by the patient especially for applications in which the extended use is of a few days or more. Cannula insertion configurations using a needle are per se known in the art and do not need to be described further in the present application. In the fully tilted park position, in the soft cannula variant, the pump may be configured to rotate in either directions R+ or R−, to effect the pumping action, the engagement end of the lever being rotated away from the catch so that it is no long in contact with the rim of the rotary actuator. In this regard, the upper suspension 37 may be configured to elastically engage an upper wall portion such that the tilt angle is increased by the elastic force of the suspension in the fully retracted position to completely disengage the engagement end 35 from the catch of the rotary actuator. In this instance, the rotary actuator may be configured to be rotated in either of the directions for the pumping action depending on the arrangement of the pump inlets and outlets.

LIST OF FEATURES ILLUSTRATED

Drug delivery device 1
  Delivery unit 2 (disposable part)
    Drug cartridge 3
    Housing 5
      Base wall 14
        Upper surface portion 48
        Mounting surface 38
          adhesive layer
          Peel off protective film 39
      Needle support guide 15
        Translation guide rails 16
        Anti-rotation guide surface 17
      Needle outlet 18
        Septum 19
      Liquid supply conduit 45
      Liquid delivery conduit 46
        Fluidic connector 52
      Needle tip locking element 50, 150
        Locking protrusion 50
        Locking nest 150
          Locking nest wall 151
    Pump module 6
      Rotor 20
      Stator 21
        Inlet 22
        Outlet 23
    Subcutaneous delivery mechanism 7
      Needle 24
      Needle support 8
        Translation guide member 12
          Guide rails 43
          Rotation body support 44
        Rotation guide member 13
          Body 47
          Pivot support 25
          Rotation axis A1
          Abutment shoulders 26
          Lower abutment shoulder 26a
          Upper abutment shoulder 26b
          Upper stop 49
          Anti-rotation guide surface 27
      Needle actuation mechanism 9
        Rotary actuator 10
          Rim 28
          Catch 29
          Recess/notch 30
          Catch edges 31
          Upper catch edge 31b
          Lower catch edge 31a
          Coupling interface 32
        Engagement lever 11
          Pivot portion 33
          Rotation axis A2
          Engagement arm 34
          Engagement end 35
          Protuberance 51
          lower suspension arm 36
          upper suspension (arm) 37
            rounded end 37a
  Base unit 4 (reusable part)
    Electronic control system
    Power source (battery)
    Pump drive
      Coupling interface
    Status indicators 40
    User interface (control buttons) 42

The invention claimed is:

1. A drug delivery device comprising a delivery unit receiving a drug cartridge containing a drug to be administered to a patient in need thereof, the delivery unit comprising a subcutaneous delivery mechanism including a needle, a needle support to which the needle is mounted, and a needle actuation mechanism configured to move the needle from a retracted position within a housing of the delivery unit, to an extended delivery position where the needle projects through a base wall of the housing, the needle actuation mechanism comprising a rotary actuator configured to engage an engagement lever coupled to the needle support for translating the needle support between the retracted position and the extended delivery position, characterized in that the needle support comprises a translation guide member slidably mounted with respect to the housing, and a rotation guide member rotatably mounted to the translation guide member, the needle being fixed to the rotation guide member configured to tilt the needle in a fully retracted park position after full retraction of the needle.

2. The device according to claim 1, wherein the engagement lever is pivotally mounted on the needle support and elastically engages the needle support configured to allow the engagement lever to elastically pivot and bias against the rotary actuator of the needle actuation mechanism in the extended delivery position such that the rotary actuator may turn freely in a delivery direction (R+).

3. The device according to claim 1, wherein the rotary actuator is coupled directly to a rotor of a pump module mounted in the delivery unit.

4. The device according to claim 3, wherein the rotary actuator is integrally formed with the rotor of the pump module.

5. The device according to claim 1, wherein the rotary actuator comprises a disc shape with an outer peripheral rim comprising a catch formed by a recess in the rim for engaging an engagement end of the engagement lever.

6. The device according to claim 1, wherein the engagement lever comprises a suspension engaging the needle support allowing elastic pivoting of the engagement lever relative to the needle support.

7. The device according to claim 1, wherein the rotation guide member comprises a cylindrical body portion rotatably mounted in a rotation member support of the translation guide member.

8. The device according to claim 1, wherein the rotation guide member of the needle support comprises a liquid channel therein interconnecting a liquid delivery conduit connected to an outlet of a pump module to the needle.

9. The device according to claim 1, wherein the engagement lever comprises a protuberance on a lower side of an engagement end configured for catching on a lower catch edge of the rotary actuator when it moves in a reverse direction (R−).

10. The device according to claim 1, wherein the engagement lever comprises a pivot portion and an engagement arm extending from the pivot portion to an engagement end, the pivot portion being mounted on a pivot support extending from the rotation guide member of the needle support.

11. The device according to claim 1, wherein the rotation guide member of the needle support comprises an anti-rotation guide surface slidably engaging a complementary anti-rotation guide surface extending from the housing base wall configured for preventing rotation of the rotation guide member when travelling between the retracted position and the extended delivery position, the anti-rotation surfaces arranged to disengage in the fully retracted park position when the rotary actuator is rotated in a reverse direction to allow tilting of the needle into the fully retracted park position preventing further reuse of the needle.

12. The device according to claim 1, wherein the rotary actuator comprises a drive interface configured for coupling to a drive mounted in a base unit comprising an electronic control system, a power source and said drive for actuation of the rotary actuator.

13. The device according to claim 1, wherein the delivery unit is formed as a disposable part containing said drug cartridge in the housing of the delivery unit, and a base unit formed as a reusable part comprising an electronic control system, a power source, and a pump drive, the base unit being removable mountable to the delivery unit.

14. The device according to claim 1, comprising a locking element engaging a tip of the needle in the fully retracted park position to block the needle in the fully retracted park position.

15. The device according to claim 14, wherein the locking element comprises a locking nest filled with a soft material into which the tip of the needle buries when moving into the fully retracted park position.

16. The device according to claim 14, wherein the locking element comprises a locking protrusion provided with a tapered surface to guide the needle tip over the locking protrusion.

17. A drug delivery device comprising a delivery unit receiving a drug cartridge containing a drug to be administered to a patient in need thereof, the delivery unit comprising a subcutaneous delivery mechanism including a needle, a needle support to which the needle is mounted, and a needle actuation mechanism configured to move the needle from a retracted position within a housing of the delivery unit, to an extended delivery position where the needle projects through a base wall of the housing, the needle actuation mechanism comprising a rotary actuator configured to engage an engagement lever coupled to the needle support for translating the needle support between the retracted position and the extended delivery position, wherein the engagement lever is pivotally mounted on the needle support and elastically engages the needle support configured to allow the engagement lever to elastically pivot and bias against the rotary actuator of the needle actuation mechanism in the extended delivery position such that the rotary actuator may turn freely in a delivery direction (R+), wherein the needle support comprises a translation guide member slidably mounted with respect to the housing, and a rotation guide member rotatably mounted to the translation guide member, the needle being fixed to the rotation guide member configured to tilt the needle in a fully retracted park position after full retraction of the needle.

18. The device according to claim 17, wherein the rotary actuator is coupled directly to a rotor of a pump module mounted in the delivery unit.

19. The device according to claim 17, wherein the rotary actuator comprises a disc shape with an outer peripheral rim comprising a catch formed by a recess in the rim for engaging an engagement end of the engagement lever.

20. The device according to claim 17, wherein the engagement lever comprises a suspension engaging the needle support allowing elastic pivoting of the engagement lever relative to the needle support.

21. The device according to claim 17, wherein the rotation guide member comprises a cylindrical body portion rotatably mounted in a rotation member support of the translation guide member.

22. The device according to claim 17, wherein the rotation guide member of the needle support comprises a liquid channel therein interconnecting a liquid delivery conduit connected to an outlet of a pump module to the needle.

23. The device according to claim 17, wherein the engagement lever comprises a protuberance on a lower side of an engagement end configured for catching on a lower catch edge of the rotary actuator when it moves in a reverse direction (R−).

24. The device according to claim 17, wherein the engagement lever comprises a pivot portion and an engagement arm extending from the pivot portion to an engagement end, the pivot portion being mounted on a pivot support extending from the rotation guide member of the needle support.

25. The device according to claim 17, wherein the rotation guide member of the needle support comprises an anti-rotation guide surface slidably engaging a complementary anti-rotation guide surface extending from the housing base wall configured for preventing rotation of the rotation guide member when travelling between the retracted position and the extended delivery position, the anti-rotation surfaces arranged to disengage in the fully retracted park position when the rotary actuator is rotated in a reverse direction to allow tilting of the needle into the fully retracted park position preventing further reuse of the needle.

26. The device according to claim 17, wherein the rotary actuator comprises a drive interface configured for coupling to a drive mounted in a base unit comprising an electronic control system, a power source and said drive for actuation of the rotary actuator.

27. The device according to claim 17, wherein the delivery unit is formed as a disposable part containing said drug cartridge in the housing of the delivery unit, and a base unit formed as a reusable part comprising an electronic control system, a power source, and a pump drive, the base unit being removable mountable to the delivery unit.

28. The device according to claim 17, comprising a locking element engaging a tip of the needle in the fully retracted park position to block the needle in the fully retracted park position.

* * * * *